United States Patent
Yawata (10) Patent No.: US 9,259,204 B2
(45) Date of Patent: Feb. 16, 2016

(54) ULTRASOUND DIAGNOSTIC APPARATUS AND METHOD OF DISPLAYING MEDICAL IMAGE THEREOF

(75) Inventor: Tsutomu Yawata, Tokyo (JP)

(73) Assignee: General Electric Company, Schenectady, NY (US)

( * ) Notice: Subject to any disclaimer, the term of this patent is extended or adjusted under 35 U.S.C. 154(b) by 754 days.

(21) Appl. No.: 13/483,507

(22) Filed: May 30, 2012

(65) Prior Publication Data

US 2012/0310092 A1 Dec. 6, 2012
US 2013/0184585 A9 Jul. 18, 2013

(30) Foreign Application Priority Data

May 30, 2011 (JP) .................................. 2011-120467

(51) Int. Cl.
*A61B 8/00* (2006.01)
*A61B 8/08* (2006.01)

(52) U.S. Cl.
CPC . *A61B 8/00* (2013.01); *A61B 8/463* (2013.01); *A61B 8/464* (2013.01); *A61B 8/466* (2013.01); *A61B 8/5261* (2013.01); *A61B 8/483* (2013.01)

(58) Field of Classification Search
USPC ................... 600/407, 437, 443–447; 382/128
See application file for complete search history.

(56) References Cited

U.S. PATENT DOCUMENTS

| | | | |
|---|---|---|---|
| 6,605,040 B2 | 8/2003 | Yawata et al. | |
| 7,720,520 B2 | 5/2010 | Willis | |
| 2002/0087075 A1 | 7/2002 | Bucholz | |
| 2006/0184019 A1 | 8/2006 | Ito et al. | |
| 2007/0167801 A1 | 7/2007 | Webler et al. | |
| 2008/0019580 A1* | 1/2008 | Ohyu et al. | 382/130 |
| 2008/0033240 A1 | 2/2008 | Hoffman et al. | |
| 2009/0131792 A1 | 5/2009 | Yawata | |
| 2009/0264758 A1* | 10/2009 | Fujita et al. | 600/443 |
| 2009/0306504 A1* | 12/2009 | Arai et al. | 600/443 |
| 2010/0217126 A1 | 8/2010 | Yawata et al. | |

FOREIGN PATENT DOCUMENTS

| | | |
|---|---|---|
| JP | 2004-016268 | 1/2004 |
| JP | 2004-105638 | 4/2004 |
| WO | 2004098414 A1 | 11/2004 |

\* cited by examiner

*Primary Examiner* — Joel F Brutus (57) ABSTRACT

An ultrasound diagnostic apparatus is provided. The ultrasound diagnostic apparatus includes an input device configured to receive an input to display a cross-section of a reference medical image, wherein the reference medical image identifies a location of the cross-section in relation to a subject, and includes a characteristic region, and a reference medical image display control device configured to display the cross-section of the reference medical image based on volume data of the reference medical image previously acquired, the cross-section displayed according to the input.

13 Claims, 8 Drawing Sheets

FIG. 12

ULTRASOUND DIAGNOSTIC APPARATUS AND METHOD OF DISPLAYING MEDICAL IMAGE THEREOF

CROSS REFERENCE TO RELATED APPLICATIONS

This application claims the benefit of Japanese Patent Application No. 2011-120467 filed May 30, 2011, which is hereby incorporated by reference in its entirety.

BACKGROUND OF THE INVENTION

The present invention relates to an ultrasound diagnostic apparatus displaying an ultrasound image and a reference medical image. The present invention also relates to a method of displaying a medical image thereof.

A conventional ultrasound diagnostic apparatus can display a real-time ultrasound image based on an echo signal acquired by transmitting an ultrasound wave from an ultrasound probe. For example, WO2004-098414 discloses an ultrasound diagnostic apparatus which displays a real-time ultrasound image and a reference medical image such as an X-ray CT (Computed Tomography) image and an MRI (Magnetic Resonance Imaging) image of the same cross-section in relation to a subject.

This ultrasound diagnostic apparatus identifies a region corresponding to a location of an ultrasound image and displays the reference medical image for the corresponding region in the volume data acquired by an X-ray CT apparatus and an MRI apparatus based on the location of an ultrasound probe detected by a location sensor. Thus, whenever the ultrasound probe is moved, the reference medical image and the ultrasound image are automatically and constantly displayed so as to follow the moving ultrasound probe. Therefore, the ultrasound image and the reference medical image can be easily compared.

However, in order to automatically display the real-time ultrasound image and the same reference medical image, it is necessary to identify a location relationship between an ultrasound image and a reference medical image about the coordinate systems. Therefore, a location alignment is performed to determine a location relationship between an ultrasound image and a reference medical image about the coordinate systems.

Hereinafter an example of aligning a location is explained. First, an arbitrary cross-section of a reference medical image is displayed by operating an operation device based on volume data of the reference medical image previously acquired from a subject. Ultrasound waves are transmitted to a subject, their echoes are received and a real-time ultrasound image of arbitrary cross-section is displayed.

Then, the operator tries to compare the real-time ultrasound image and the reference medical image, and moves the location of an ultrasound probe, and operates the operation device. Then the same cross-sections of the ultrasound image and the reference medical image finally are displayed. At this time, the displayed ultrasound image and reference medical image are the cross-sectional images of a characteristic portion, such as a branched region of blood vessel. Once the same cross-sections of the ultrasound image and the reference medical image are displayed, the operator indicates the characteristic portions of the ultrasound image and the reference medical image that seems to be indicating the same location on the subject with a cursor. Thus, the same portions of the coordinate systems of the ultrasound image and the reference medical image are identified, and the location relationship between the ultrasound image and the reference medical image about the same coordinate system is identified.

When the ultrasound diagnostic apparatus operator who is unaccustomed to the X-ray CT image or the MRI image performs such location alignment, one may not be able to grasp which section in the subject a reference medical image is even if the reference medical image is displayed. In some cases, finding a cross-section of the reference medical image having a characteristic region for location alignment takes a longer time, and displaying the same cross-sections of the reference medical image and the ultrasound image takes a longer time.

BRIEF DESCRIPTION OF THE INVENTION

In one aspect, an ultrasound diagnostic apparatus is provided. The ultrasound diagnostic apparatus includes an input device for inputting a command for displaying a cross-section of a reference medical image, including a characteristic region, which identifies a location of the cross-section in relation to a subject. The apparatus includes a reference medical image display control device for displaying the reference medical image about the cross-section inputted by an input device based on the volume data of the reference medical image.

In one embodiment, the ultrasound diagnostic apparatus includes a marker display control device for displaying a marker for indicating a location on a subject about the cross-section of the displayed reference medical image.

Further, in one embodiment, the ultrasound diagnostic apparatus includes a distance display control device for displaying the distance between the location of the cross-section of the reference medical image of the subject and the location of the cross-section of the ultrasound image of the subject.

When an operator inputs a command for displaying a reference medical image, including a characteristic region, in which the location on a subject is identified, a cross-section of the reference medical image thereof is displayed. Since the cross-section of the reference medical image is displayed in which the relative location on subject is identified, a cross-section of a real-time ultrasound image having the same cross-section as the reference medical image can be easily displayed. Therefore, the location can be easily aligned.

Also, the cross-section in which the reference medical image is displayed in relation to the subject can be easily identified by referring to the marker.

Further, a portion of the cross-section of the reference medical image in relation to the subject can be easily identified by referring to the displayed distance.

Further objects and advantages will be apparent from the following description of exemplary embodiments as illustrated in the accompanying drawings.

DETAILED DESCRIPTION OF THE INVENTION

Hereinafter, exemplary embodiments are explained with reference to FIG. 1 through FIG. 8. An ultrasound diagnostic apparatus 1 shown in FIG. 1 includes an ultrasound probe 2, a transmitting/receiving device 3, an echo data processing device 4, a display control device 5, a display device 6, an operation device 7, a controller 8 and a HDD (Hard Disk Drive) 9.

Figure 1:
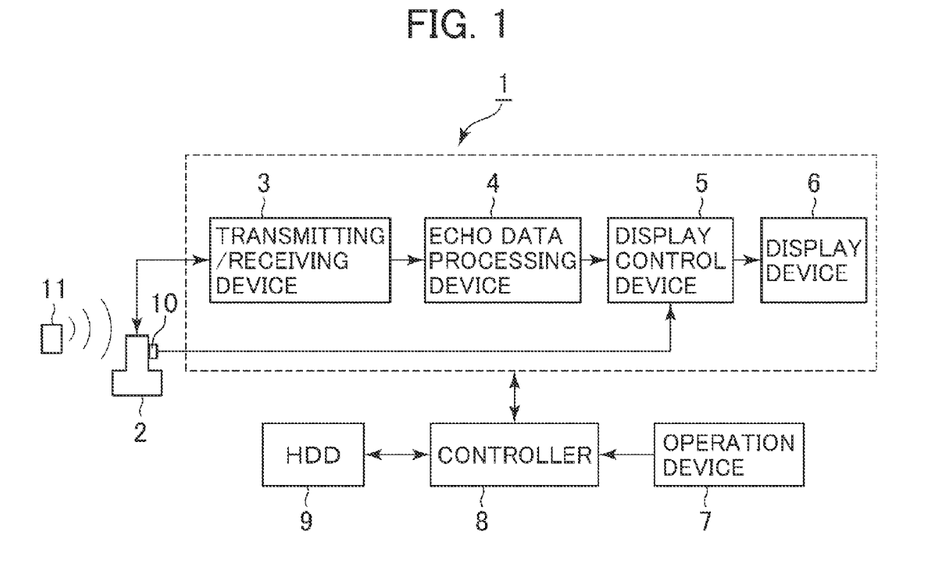
FIG. 1 is a block diagram showing one example of a configuration of an ultrasound diagnostic apparatus.

The ultrasound probe 2 is configured with an array of ultrasound transducers (not shown), and the ultrasound transducers transmit ultrasound waves to a subject and receive their echo signals.

The magnetic sensor 10 includes Hall elements and is provided on the ultrasound probe 2, for example. Magnetic field generated from the magnetic field generation device 11 including a magnetic field generation coil is detected by the magnetic sensor 10. The signal detected at the magnetic sensor 10 is inputted to the display control device 5. The signal detected at the magnetic sensor 10 can be inputted to the display control device 5 via a cable that is not illustrated, or can be inputted to the display control device 5 wirelessly. The magnetic field generation device 11 and the magnetic sensor 10 are used to detect a location and a tilt of the ultrasound probe 2.

The transmitting/receiving device 3 supplies an electric signal for transmitting an ultrasound wave from the ultrasound probe 2 in a predetermined scan condition based on a control signal from the controller 8. Also, the transmitting/receiving device 3 performs a signal processing, such as A/D conversion and phase/adding process for the acquired echo signal by the ultrasound probe 2, and then outputs the processed echo data to the echo data processing device 4.

The echo data processing device 4 performs a predetermined process to the echo data outputted from the transmitting/receiving device 3. For example, the echo data processing device 4 generates B-mode data by performing a B-mode process, such as a logarithmic compression process or an envelope demodulation process.

Figure 2:
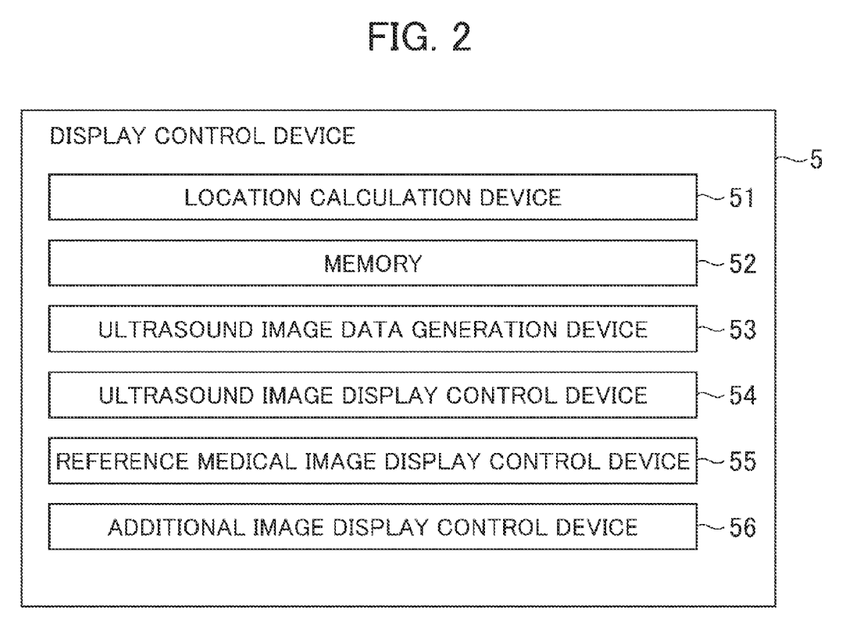
FIG. 2 is a block diagram showing one configuration of a display control device of an ultrasound diagnostic apparatus in the first embodiment.

As shown in FIG. 2, the display control device 5 has a location calculation device 51, a memory 52, an ultrasound image data generation device 53, an ultrasound image display control device 54, a reference medical image display control device 55 and an additional image display control device 56. The location calculation device 51 calculates the location and tilt information of the ultrasound probe 2 in the coordinate system of three-dimensional space based on the magnetic detection signal from the magnetic sensor 10 and with the magnetic field generation device 11 as a point of origin. Further, the location calculation device 51 calculates the location information of echo data in the coordinate system of three-dimensional space based on the probe location. The coordinate system of three-dimensional space with the magnetic field generation device 11 as the point of origin is referred as a coordinate system of the ultrasound image UG.

The memory 52 includes a semiconductor memory, such as RAM (Random Access Memory) or ROM (Read Only Memory). For example, the memory 52 stores the data outputted from the echo data processing device 4, which will be converted to the ultrasound image data in the ultrasound image data generation device 53. The data before being converted to the ultrasound image data is referred as raw data. The raw data can be stored in the HDD 9.

Also, volume data of the reference medical image RG previously acquired are stored in the memory 52. The volume data can be stored in the HDD 9. The volume data including the location information of the coordinate system of the reference medical image RG are stored in the memory 52 and the HDD 9.

The reference medical image RG is a medical image other than the ultrasound images. Specifically, the reference medical image RG is an X-ray CT image or an MRI image previously acquired by the X-ray CT apparatus or the MRI apparatus.

The ultrasound image data generation device 53 converts the data inputted from an echo data processing device 4 by a scan converter, and generates the ultrasound image data.

The ultrasound image display control device 54 displays a real-time ultrasound image UG based on the ultrasound image data.

The reference medical image display control device 55 performs a reference medical image display control function. Specifically, the reference medical image display control device 55 displays the reference medical image RG corresponding to the location of the echo signal calculated by the location calculation device 51. As explained later, the reference medical image display control device 55 displays the cross-section of the reference medical image RG which was inputted from the operation device 7 based on the volume data.

As explained later, the additional image display control device 56 displays the body mark BM on the display device 6 as well as the probe mark PM on the body mark BM (see FIG. 5).

The display device 6 includes a LCD (liquid crystal display) or a CRT (Cathode Ray Tube). The operation device 7 includes a keyboard and a pointing device (not illustrated) for an operator to command or input information.

The controller 8 includes a CPU (Central Processing Unit). The controller 8 reads out the control program stored in the HDD 9 and executes functions at respective devices in the ultrasound diagnostic apparatus 1.

Figure 3:
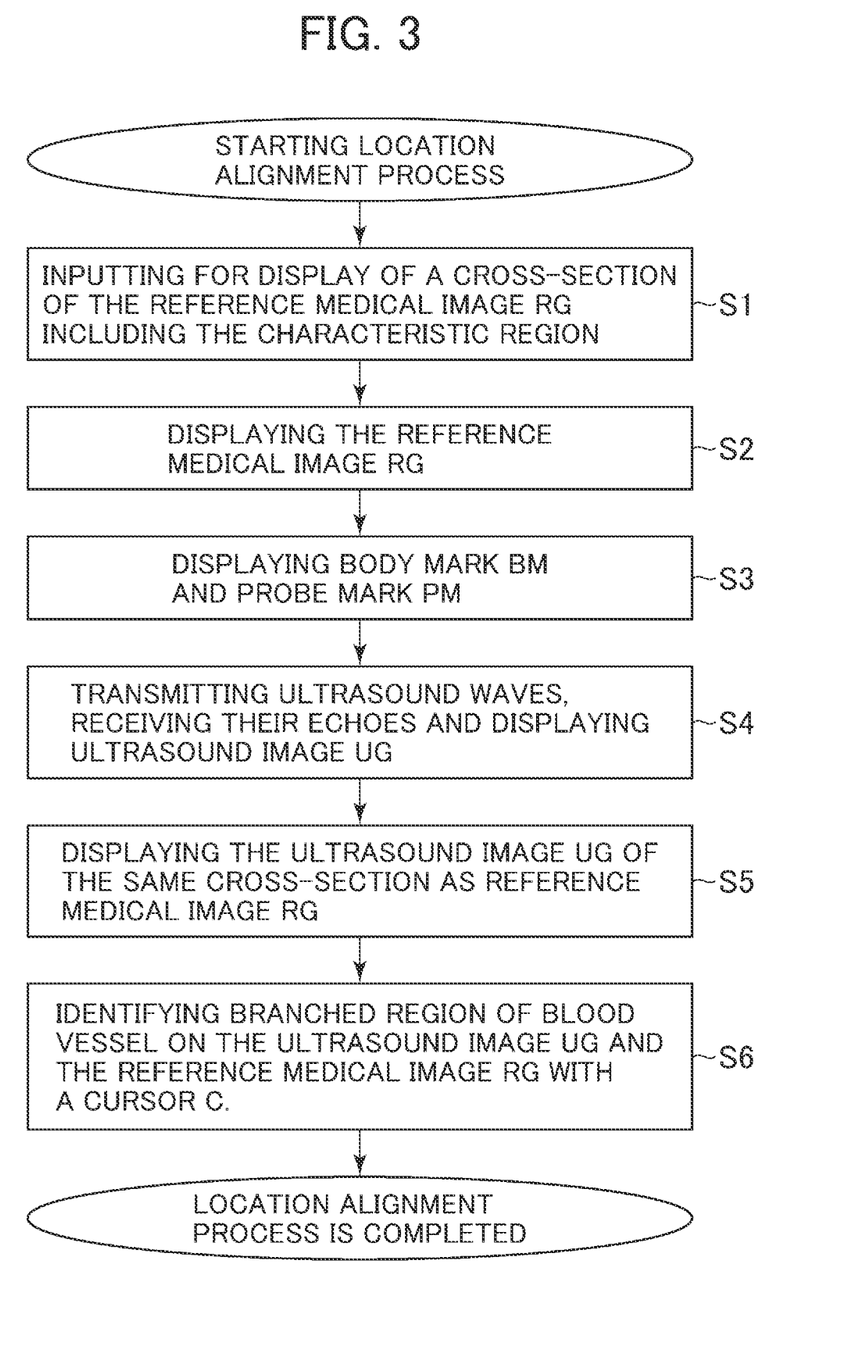
FIG. 3 is a flow-chart showing operation of an ultrasound diagnostic apparatus in the first embodiment.

An operation of the ultrasound diagnostic apparatus 1 is explained based on a flow-chart shown in FIG. 3. The operation explains the alignment process of the coordinate system of the ultrasound image UG and the reference medical image RG.

First, in step S1 of FIG. 3, the operator performs the input for displaying a cross-section of the reference medical image RG, including the characteristic region, on the operation device 7. Specifically, the additional image display control device 56 displays a plurality of candidate cross-sections on the display device 6. Then, the operator inputs a cross-section to display among the candidate cross-sections by operating a track ball and selecting by a cursor on the operation device 7.

Here, the candidate cross-sections that are displayed are previously stored in the volume data of the reference medical image RG, and locations on a subject is assumed to be identified. For example, the cross-sections of a branched region of a blood vessel (such as a branched region between a main portal vein and a horizontal portion of left hepatic) are stored as the characteristic regions of volume data of a liver. The additional image display control device 56 displays the stored candidate cross-sections on the display device 6 with icons or letters.

Figure 4:
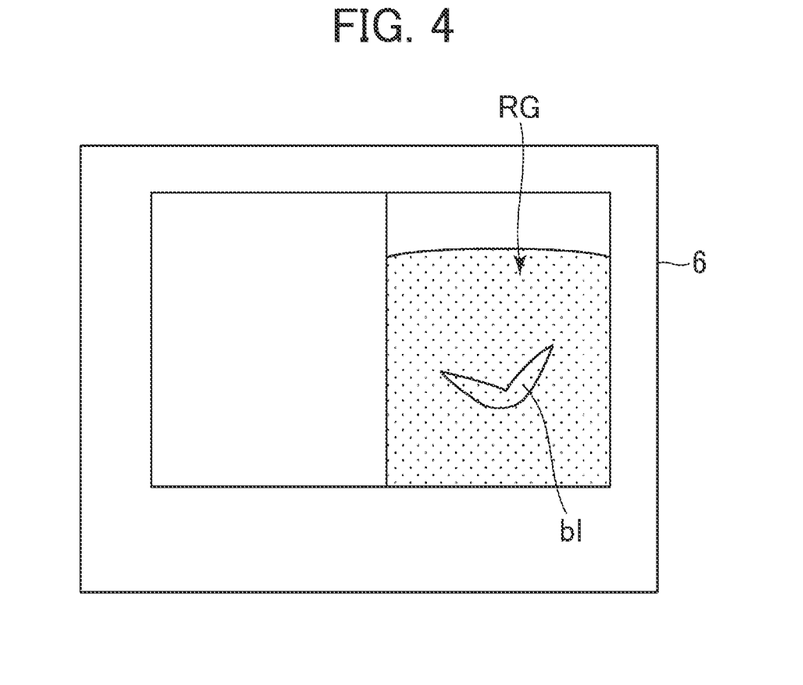
FIG. 4 is a drawing showing a display device displaying a reference medical image.

In step S2, the reference medical image display control device 55 displays the cross-section of reference medical image RG selected in the step S1 on the display device 6, as shown in FIG. 4. In FIG. 4, the symbol b1 indicates a blood vessel.

Figure 5:
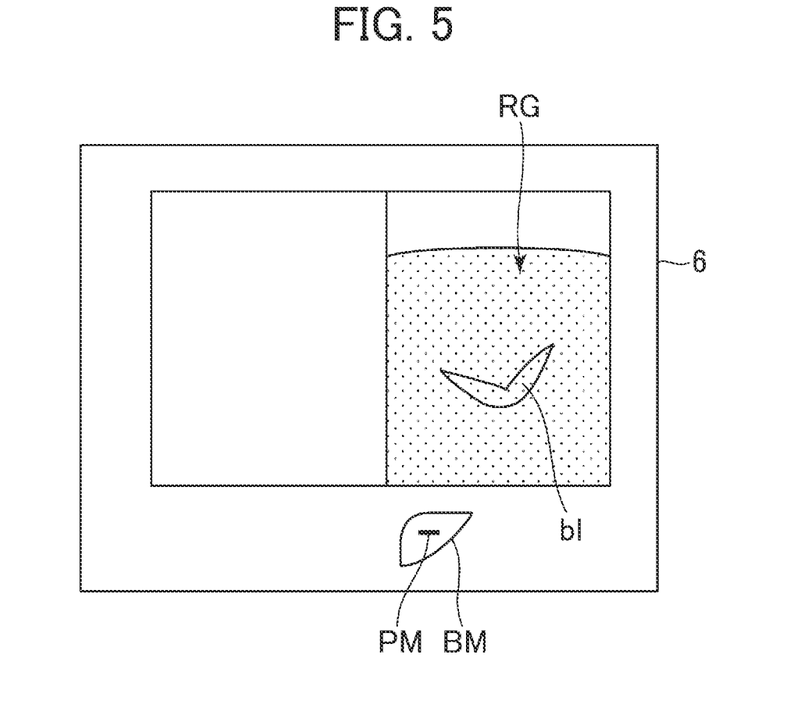
FIG. 5 is a drawing showing a display device showing a body mark and a probe mark.

In step S3, as shown in FIG. 5, the additional image display control device 56 displays the body mark BM and the probe mark PM on the display device 6. In this example, the body mark BM indicates a liver. The probe mark PM displayed on the body mark BM indicates a location of a cross-section in relation to a subject selected in step S2.

The location of the probe mark PM on the body mark BM is stored for each cross-section of the reference medical image RG. In step S3, a probe mark PM corresponding to the location of the cross-section selected in step S2 is displayed.

Incidentally, the body mark BM and the probe mark PM can be displayed simultaneously with the display of the reference medical image RG in step S2.

Figure 6:
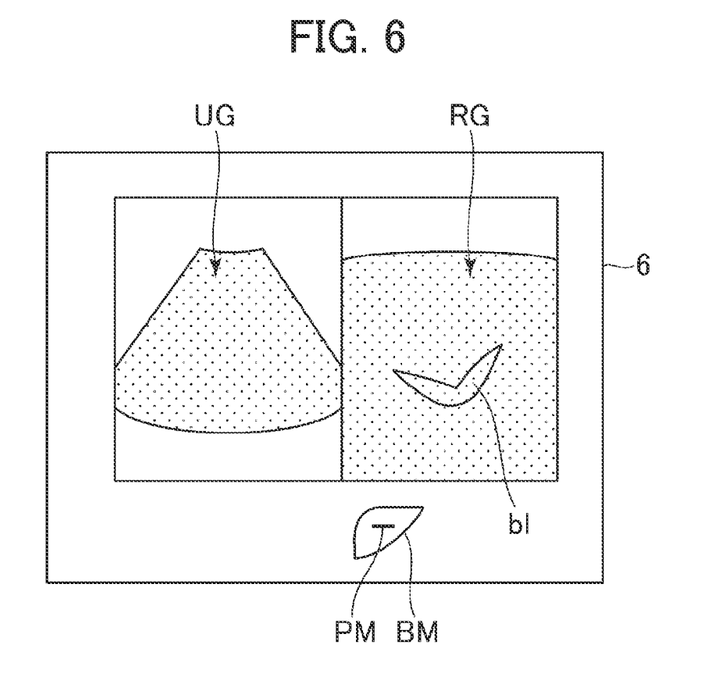
FIG. 6 is a drawing showing one example of a display device showing an ultrasound image along with a reference medical image.

In step S4, transmitting/receiving of ultrasound is performed by contacting the ultrasound probe 2 on the surface of a body of a subject. Then, as shown in FIG. 6, the ultrasound image display control device 54 displays the ultrasound image UG on the display device 6, which is generated based on the echo signal. The ultrasound image UG is, for example, a B-mode image. The ultrasound image UG is displayed on the display device 6 and side-by-side with the reference medical image RG. Additionally, the cross-sections of the ultrasound image UG and the reference medical image RG are presumed to be parallel.

Figure 7:
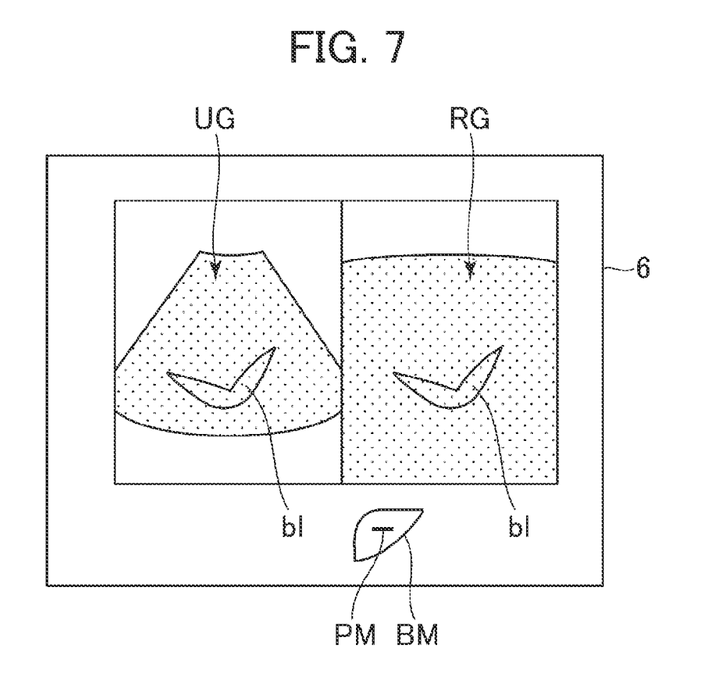
FIG. 7 is one example of a display device showing an ultrasound image about a cross-section of a reference medical image.

Once the ultrasound image UG is displayed in step S4, in step S5, the operator moves the ultrasound probe 2 and displays the same cross-section of the ultrasound UG as the reference medical image, as shown in FIG. 7. By referring to the probe mark PM, the operator can easily recognize as to where the ultrasound probe 2 should be positioned on the subject, and thus the same cross-section as the reference medical image RG can be easily detected.

Figure 8:
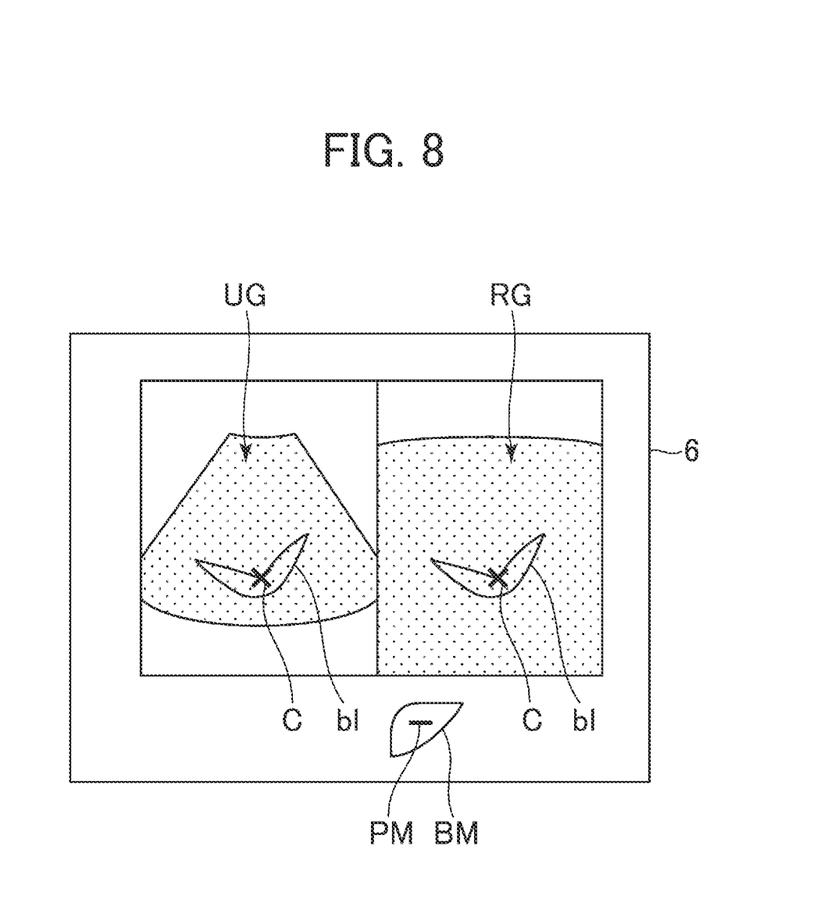
FIG. 8 is a drawing of an example of a display device in which the same portion is indicated on the ultrasound image and the reference medical image using a cursor.

Once the ultrasound image UG about the same cross-section as the reference medical image RG is displayed in step S5, in step S6, the operator indicates portions of the ultrasound image UG and the reference medical image RG that are assumed to be the same portion with a cursor C, as shown in FIG. 8. In the FIG. 8, the branched region of the blood vessel b1 is indicated with the cursor C. Specifically, the operator moves the cursor C displayed above the ultrasound image UG and the reference medical image RG with the operation device 7 such as a track ball, and selects the branched region of the blood vessel.

Here, data of the reference medical image RG includes location information. Therefore, by selecting portions of the ultrasound image UG and the reference medical image RG that are assumed as the same portions, the coordinate system of the ultrasound image UG and the corresponding coordinate system of the reference medical image RG can be identified. Thus, the coordinate systems of the ultrasound image UG and the reference medical image RG can be converted. Thus, the respective locations are aligned and the reference medical image display control device 55 displays the reference medical image RG by identifying a location corresponding to the echo signal location calculated by the location calculation device 51 in volume data. Thus, on the display device 6, the same cross-section of reference medical image RG is displayed so as to follow the real-time ultrasound image UG.

According to the ultrasound diagnostic apparatus 1 of the present embodiment explained above, since the cross-section of the reference medical image RG selected by the operator is displayed during the location alignment process and the location in relation to the subject is identified, a process of searching a cross-section of the reference medical image RG for location alignment, including the characteristic region, becomes unnecessary. Therefore, the operator can easily identify the cross-section to display as the ultrasound image UG on the subject, or the same cross-section as the reference medical image RG, in a relatively short time. Since the same cross-sections of the ultrasound image UG and the reference medical image RG are displayed relatively easily, a location alignment process can be easily performed.

Also, since the body mark BM and the probe mark PM are displayed in step S3, the operator can easily display the ultrasound image UG having the same cross-section as the reference medical image RG by moving the ultrasound probe 2 along the markings.

Next, a second embodiment is explained. In the explanation below, contents that are different from the first embodiment are explained.

Figure 9:
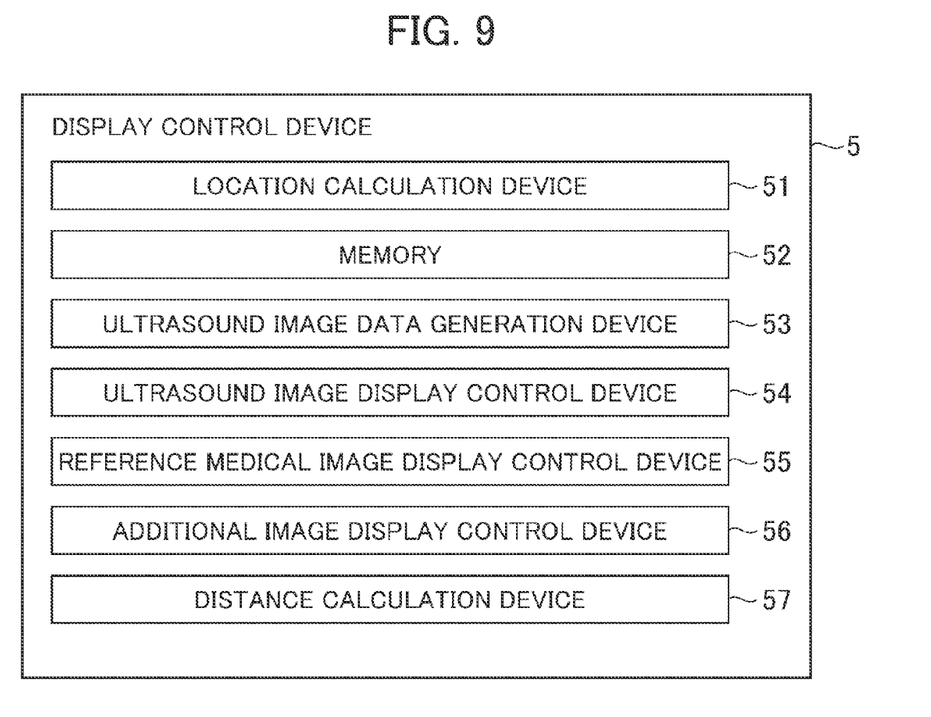
FIG. 9 is a block diagram showing a configuration of a display control device of an ultrasound diagnostic apparatus in the second embodiment.

In the embodiment below, as shown in FIG. 9, the display control device 5 has a location calculation device 51, a memory 52, an ultrasound image data generation device 53, an ultrasound image display control device 54, a reference medical image display control device 55, an additional image display control device 56 and a distance calculation device 57. The distance calculation device 57 is explained below.

Figure 10:
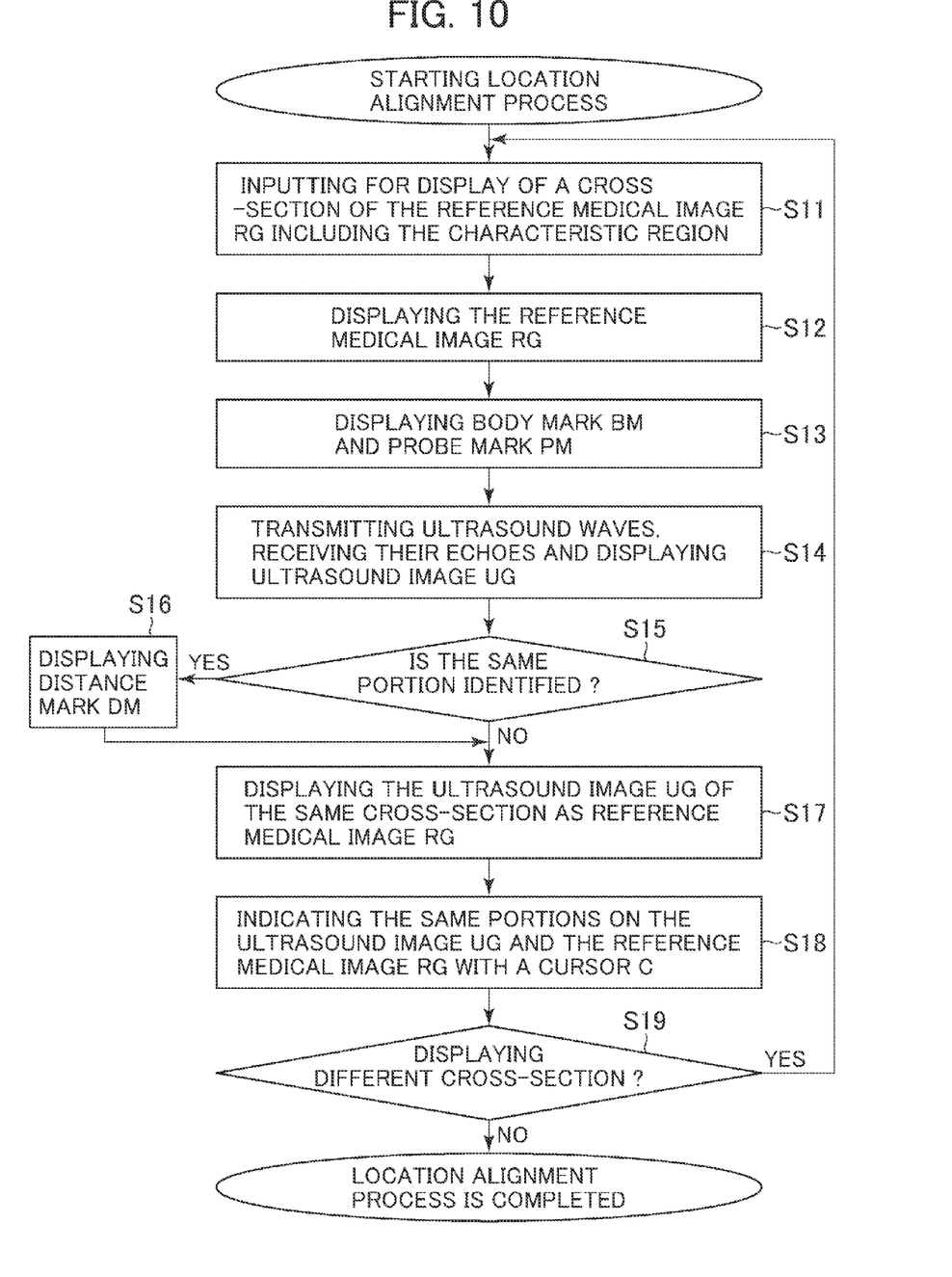
FIG. 10 is a flow-chart showing operation of the second embodiment.

An operation of the second embodiment is explained based on the flow-chart in FIG. 10. In this embodiment, a plurality of cross-sections can be indicated on the ultrasound image UG and the reference medical image RG with a cursor C. By identifying the corresponding locations between the ultrasound image UG and the reference medical image RG about the plurality of cross-sections, location alignment becomes more precise.

The steps are explained in detail. Steps S11 to S14 are the same process as the steps S1 to S4 previously explained. When the ultrasound image UG is displayed in step S14, in step S15, the controller 8 determines whether or not the same portions of the ultrasound image UG and reference medical image RG are indicated. The indication of the same portion is a process in step S18.

If the same portions are not indicated in step S15, ("no" in step S15), then proceeds to step S17. On contrary, if the same portions indicated in step S15 ("yes" in step S15), then proceeds to step S16.

Figure 11:
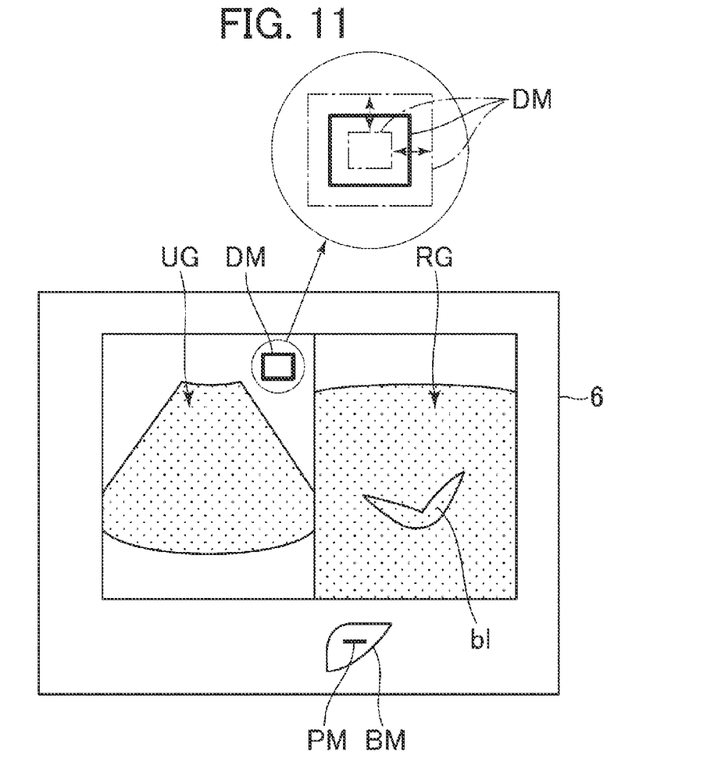
FIG. 11 is a drawing showing one example of a display device indicating a distance mark.

In step S16, as shown in FIG. 11, the additional image display control device 56 displays a distance mark DM on the display device 6. The distance mark DM displays the distance D between a location of the cross-section of the ultrasound image UG in relation to the subject displayed in step S14 (location of the transmitting/receiving surface of the ultrasound) and a location of the cross-section of a reference medical image RG in relation to the subject displayed in step S12.

The distance D is calculated by the distance calculation device 57. Specifically, the distance calculation device 57 identifies a location corresponding to the location of the cross-section of the ultrasound image UG calculated by the location calculation device 51, in the volume data of the reference medical image RG. Here, since the corresponding locations about the coordinate systems of the ultrasound image UG and the reference medical image RG are identified, coordinate systems of the ultrasound image UG and the reference medical image RG can be converted. The location corresponding to the cross-section of the ultrasound image UG can be identified in a volume data of the reference medical image RG.

Once the location of the cross-section of the ultrasound image UG is identified in the volume data of the reference medical image RG in such manner, the distance calculation device 57 calculates the distance D between the cross-sections of the ultrasound image UG and the reference medical image RG.

The additional image display control device 56 displays the distance mark DM based on the distance D calculated by the distance calculation device 57. In this present embodiment, the distance mark DM is a rectangular shape having an area corresponding to the distance D. An area of the distance mark DM becomes larger as the distance D becomes longer, and becomes smaller as the distance D becomes smaller.

Figure 12:
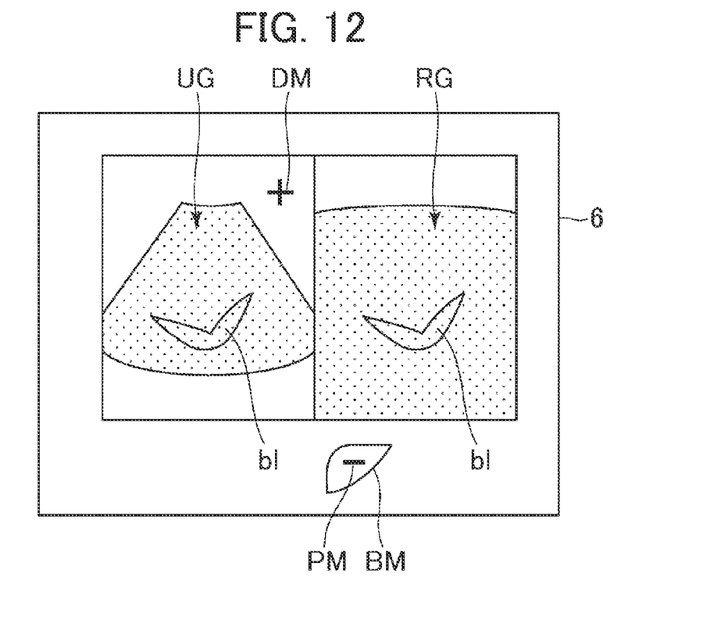
FIG. 12 is an example of a display device showing a distance mark of when the reference medical image and the ultrasound image about the same cross-section are displayed.

However, whenever the distance D is zero, or the ultrasound image UG and the reference medical image RG about the same cross-sections are displayed, the distance mark DM becomes a "+" mark (see FIG. 12).

If the distance mark DM is displayed in the step S16 or if the determination was "no" (in other words, if the same portion is determined to be not indicated), the step S17 is processed and the ultrasound image UG having the same cross-section as the reference medical image RG is displayed. If the distance mark DM is displayed in step S16, an identification of the same cross-section of the reference medical image RG becomes much easier by an operator referring to the probe mark PM and the distance mark DM.

When the distance mark DM is displayed in step S16 and the ultrasound image UG about the same cross-section as the reference medical image RG is displayed in step S17, the distance mark DM becomes "+" mark, as shown in FIG. 12.

Next, the step S18 is processed. The step S18 is the same process as the step S6 explained above.

In step S19, the additional image display control device 56 displays a message image (not drawn) on the display device 6, questioning whether to display a different cross-sectional image or not. The operator inputs a command to display or not to display a different cross-section image on the operation device 7.

In step S19, if the command for displaying a different cross-section image is inputted ("yes" in step S19), then moves to the step S11 and repeats the step explained above. On the other hand, if the command, not to display a different cross-sectional image ("no" in step S19), is inputted, then the location alignment process is completed.

Although specific embodiments are described above, other embodiments may be configured without departing from the scope of the invention. For example, in steps S1 and S11, inputting the reference medical image RG including the characteristic region is not limited to the embodiment described above as long as it includes an input for selecting a cross-section that the operator wants to display, and a characteristic region can be inputted by letters instead.

Also, the input for displaying a reference medical image RG of a cross-section including a characteristic region is not limited to the input for selecting the cross-section that the operator wants to display, and can be an input for displaying a preset cross-section among the characteristic region in the volume data previously acquired in the reference medical image. In this case, in step S18 of the second embodiment, after identifying the cross-section of the same portion on the ultrasound image UG and the reference medical image RG, different cross-sections of the reference medical image RG can be displayed in the preset sequence.

Also, the body mark BM and the probe mark PM is only one example and is not limited to those explained in the embodiment. For example, the body mark BM can be a mark indicating a top half of a human body.

Further, if the cross-sections of the ultrasound image UG and the reference medical image RG are not parallel, corresponding locations of the ultrasound image UG and the reference medical image RG about coordinate systems can be identified for at least three different cross-sections by indicating the corresponding locations on the ultrasound image UG and the reference medical image RG using the cursor C. In this case, a reference medical image RG is displayed simultaneously for the previously stored cross-sections, the corresponding cross-sections of the ultrasound image UG is displayed and indicated with the cursor C. At this time, a corresponding body mark BM and probe mark PM can be displayed.

Many widely different embodiments of the invention may be configured without departing from the spirit and the scope of the embodiments described herein. It should be understood that the present invention is not limited to the specific embodiments described in the specification, except as defined in the appended claims.

The invention claimed is:

1. An ultrasound diagnostic apparatus comprises:
    an ultrasound probe configured to transmit ultrasound waves to a subject and receive echo signals;
    an ultrasound image display control device configured to display a real-time ultrasound image based on the received echo signals, wherein the real-time ultrasound image includes an ultrasound cross-section that includes a characteristic region of the subject;
    a location sensor configured to detect a location of the ultrasound probe;
    a location calculation device configured to calculate a first location of the echo signal in a first coordinate system of the real-time ultrasound image based on the location of the ultrasound probe;
    an input device configured to receive an input to display a reference cross-section of a reference medical image, wherein the input includes a selection of the reference cross-section of the reference medical image, by an operator, from among a plurality of reference cross-sections of reference medical images previously acquired, wherein the selected reference cross-section of the reference medical image identifies the characteristic region of the subject in the reference cross-section of the reference medical image and identifies a second location of the reference cross-section in relation to the subject, and wherein the reference medical image is a medical image other than the real-time ultrasound image; and
    a reference medical image display control device configured to display the reference cross-section of the reference medical image based on the plurality of reference cross-sections of reference medical images previously acquired, wherein the reference cross-section is displayed according to the input.

2. The ultrasound diagnostic apparatus of claim 1, further comprises:

a marker display control device configured to display a marker indicating the second location of the reference cross-section of the reference medical image in relation to the subject.

3. The ultrasound diagnostic apparatus of claim 2, further comprises:
a distance display control device configured to display a distance between the second location of the reference cross-section of the reference medical image in relation to the subject and the ultrasound cross-section of the real-time ultrasound image.

4. The ultrasound diagnostic apparatus of claim 3, wherein the input includes an input to select the reference cross-section that the operator wants to display from among the plurality of reference cross-sections of reference medical images previously acquired.

5. The ultrasound diagnostic apparatus of claim 3, wherein the input includes an input to display a preset reference cross-section of the plurality of reference cross-sections of reference medical images previously acquired.

6. The ultrasound diagnostic apparatus of claim 2, wherein the input includes an input to select the reference cross-section that the operator wants to display from among the plurality of reference cross-sections of reference medical images previously acquired.

7. The ultrasound diagnostic apparatus of claim 2, wherein the input includes an input to display a preset reference cross-section of the plurality of reference cross-sections of reference medical images previously acquired.

8. The ultrasound diagnostic apparatus of claim 1, further comprises:
a distance display control device configured to display a distance between the second location of the reference cross-section of the reference medical image in relation to the subject and the ultrasound cross-section of the real-time ultrasound image.

9. The ultrasound diagnostic apparatus of claim 8, wherein the input includes an input to select the reference cross-section that the operator wants to display from among the plurality of reference cross-sections of reference medical images previously acquired.

10. The ultrasound diagnostic apparatus of claim 8, wherein the input includes an input to display a preset reference cross-section of the plurality of reference cross-sections of reference medical images previously acquired.

11. The ultrasound diagnostic apparatus of claim 1, wherein the input includes an input to display a preset reference cross-section of the plurality of reference cross-sections of reference medical images previously acquired.

12. A method of displaying a medical image in an ultrasound diagnostic apparatus, comprising:
transmitting, by an ultrasound probe, ultrasound waves to a subject;
receiving, by the ultrasound probe, echo signals;
displaying, by an ultrasound image display control device, a real-time ultrasound image based on the received echo signals, wherein the real-time ultrasound image includes an ultrasound cross-section that includes a characteristic region of the subject;
detecting, by a location sensor, a location of the ultrasound probe;
calculating, by a location calculation device, a first location of the echo signals in a first coordinate system of the real-time ultrasound image based on the location of the ultrasound probe;
receiving an input to display a reference medical image about a reference cross-section including the characteristic region, wherein the input includes a selection of the reference cross-section of the reference medical image, by an operator, from among a plurality of reference cross-sections of reference medical images previously acquired, the selected reference cross-section of the reference medical image indicating the characteristic region of the subject in the reference cross-section of the reference medical image and indicating a second location of the reference cross-section in relation to the subject, and wherein the reference medical image is a medical image other than the real-time ultrasound image; and
displaying the reference medical image about the reference cross-section based on the plurality of reference cross-sections of reference medical images previously acquired, wherein the reference cross-section is displayed according to the input.

13. An ultrasound diagnostic apparatus comprises:
an ultrasound probe configured to transmit ultrasound waves to a subject and receive echo signals;
an ultrasound image display control device configured to display a real-time ultrasound image based on the received echo signals, wherein the real-time ultrasound image includes an ultrasound cross-section that includes a characteristic region of the subject;
a location sensor configured to detect a location of the ultrasound probe;
a location calculation device configured to calculate a first location of the echo signal in a first coordinate system of the real-time ultrasound image based on the location of the ultrasound probe;
an input device configured to receive an input to display a reference cross-section of a reference medical image, wherein the input includes selecting and displaying a preset reference medical image, by an operator, from a plurality of reference medical images, including the reference cross-section, wherein the displayed reference medical image identifies a second location of the reference cross-section in relation to the subject, and wherein the reference medical image is a medical image other than the real-time ultrasound image; and
a reference medical image display control device configured to display the reference cross-section of the preset reference medical image based on the plurality of reference medical images previously acquired, wherein the reference cross-section is displayed according to the input.

* * * * *